(12) United States Patent
Zablocki et al.

(10) Patent No.: US 6,852,723 B2
(45) Date of Patent: Feb. 8, 2005

(54) ARALKYL SUBSTITUTED PIPERAZINE COMPOUNDS

(75) Inventors: Jeff Zablocki, Mountain View, CA (US); Elfatih Elzein, Fremont, CA (US); Brent K. Blackburn, Los Altos, CA (US); Tim Marquart, Mountain View, CA (US); Prabha N. Ibrahim, Mountain View, CA (US); Venkata P. Palle, Gurgaon (IN)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 10/365,344

(22) Filed: Feb. 11, 2003

(65) Prior Publication Data

US 2003/0176440 A1 Sep. 18, 2003

Related U.S. Application Data

(63) Continuation of application No. 09/791,133, filed on Feb. 22, 2001, now Pat. No. 6,552,023.
(60) Provisional application No. 60/206,396, filed on May 23, 2000, and provisional application No. 60/184,457, filed on Feb. 22, 2000.

(51) Int. Cl.[7] ..................... A61K 31/495; A61K 31/496
(52) U.S. Cl. ............................. 514/252.12; 514/254.11; 544/377; 544/400
(58) Field of Search ............................... 544/377, 400; 514/252.12, 254.11

(56) References Cited

U.S. PATENT DOCUMENTS

| 3,710,795 A | 1/1973 | Higuchi et al. |
|---|---|---|
| 4,558,129 A | 12/1985 | Kluge et al. |
| 4,567,264 A | 1/1986 | Kluge et al. |
| 4,766,125 A | 8/1988 | Van Daele |
| 5,472,707 A | 12/1995 | Samuels et al. |
| 5,506,229 A | 4/1996 | Dow |
| 5,670,171 A | 9/1997 | Santus et al. |
| 5,906,988 A | 5/1999 | Dow |

FOREIGN PATENT DOCUMENTS

| CA | 2054544 | 5/1992 |
|---|---|---|
| EP | 0 068 544 | 1/1983 |
| EP | 0 143 016 | 5/1985 |
| EP | 0 407 780 | 1/1991 |
| EP | 0 483 932 | 6/1992 |
| JP | 03 141258 A | 6/1991 |

OTHER PUBLICATIONS

Pepine et al., "A Controlled Trial with a Novel Anti–Ischemic Agent, Ranolazine, in Chronic Stable Angina Pectoris That is Responsive to Coventional Antianginal Agents", *American Journal of Cardiology*, vol. 84, pp. 46–50 (1999).

*Primary Examiner*—Emily Bernhardt
(74) *Attorney, Agent, or Firm*—CV Therapeutics, Inc.

(57) ABSTRACT

Novel compounds of the general formula:

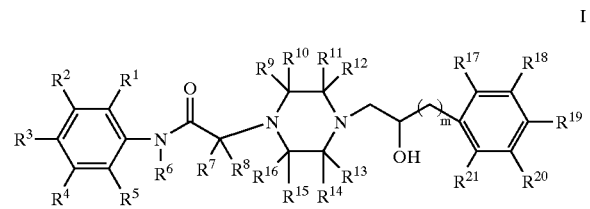

I and pharmaceutically acceptable acid addition salts thereof, wherein the compounds are useful in therapy to protect skeletal muscles against damage resulting from trauma or to protect skeletal muscles subsequent to muscle or systemic diseases such as intermittent claudication, to treat shock conditions, to preserve donor tissue and organs used in transplants, in the treatment of cardiovascular diseases including atrial and ventricular arrhythmias, Prinzmetal's (variant) angina, stable angina, and exercise induced angina, congestive heart disease, and myocardial infarction.

18 Claims, No Drawings

US 6,852,723 B2

ARALKYL SUBSTITUTED PIPERAZINE COMPOUNDS

This application is a continuation of U.S. patent application Ser. No. 09/791,133, filed Feb. 22, 2001, now issued as U.S. Pat. No. 6,552,023 which claimed priority to U.S. Application No. 60/184,457, filed on Feb. 22, 2000 and to U.S. Application No. 60/206,396, filed on May 23, 2000, the specifications of which are all incorporated herein by reference.

BACKGROUND OF THE INVENTION

1. Field of the Invention

The present invention is concerned with substituted piperazine compounds, therapeutic dosage forms including one or more of the compounds, and methods for treating diseases in mammals, and in particular, in a human in a therapy selected from the group including protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

2. Description of the Art

U.S Pat. No. 4,567,264, the specification of which is incorporated herein by reference, discloses a class of substituted piperazine compounds that includes a compound known as ranolazine, (±)-N-(2,6-dimethylphenyl)-4-[2-hydroxy-3-(2-methoxyphenoxy)-propyl]-1-piperazine-acetamide, and its pharmaceutically acceptable salts, and their use in the treatment of cardiovascular diseases, including arrhythmias, variant and exercise-induced angina, and myocardial infarction.

U.S. Pat. No. 5,506,229, which is incorporated herein by reference, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. In particular, ranolazine is particularly useful for treating arrhythmias, variant and exercise-induced angina, and myocardial infarction by partially inhibiting cardiac fatty acid oxidation. Conventional oral and parenteral ranolazine formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers.

Despite the important discovery that ranolazine is a very useful cardiac therapeutic agent, there remains a need for compounds that are partial fatty acid oxidation inhibitors that have a half-life greater than ranolazine and that have activities as least similar to ranolazine.

SUMMARY OF THE INVENTION

This invention includes novel substituted piperazine compounds that are partial fatty acid oxidation inhibitors with good therapeutic half-lives.

This invention also includes novel substituted piperazine compounds that can be administered to a mammal to protect skeletal muscles against damage resulting from trauma, to protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

This invention includes a class of substituted piperazine compounds having the following formula:

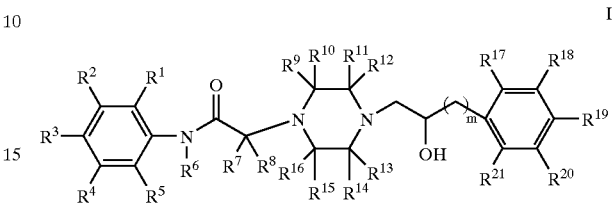

wherein m=1 or 2 or 3;

$R^1$, $R^2$, $R^3$, $R^4$, and $R^5$ are each independently selected from the group consisting of hydrogen, halo, $NO_2$, $CF_3$, CN, $OR_{23}$, $SR_{23}$, $N(R_{23})_2$, $S(O)R_{22}$, $SO_2R_{22}$, $SO_2N(R_{23})_2$, $NR_{23}CO_2R_{22}$, $NR_{23}CON(R_{23})_2$, $COR_{23}$, $CO_2R_{23}$, $CON(R_{23})_2$, $NR_{23}SO_2R_{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR_{23}$, $SR_{23}$, $N(R_{23})_2$, $S(O)R_{22}$, and $SO_2R_{22}$;

$R^6$, $R^7$ and $R^8$ each independently selected from the group consisting of hydrogen or $C_{1-15}$ alkyl;

$R^9$, $R^{10}$, $R^{11}$, $R^{12}$, $R^{13}$, $R^{14}$, $R^{15}$ and $R^{16}$ are each independently selected from the group consisting of hydrogen, $CO_2R_{23}$, $CON(R_{23})_2$, $C_{1-4}$ alkyl, or aryl wherein the alkyl and aryl substituents are optionally substituted with 1 substituent selected from the group consisting of halo, $CF_3$, CN, $OR_{23}$, $N(R_{23})_2$, $CO_2R_{23}$, $CON(R_{23})_2$ or aryl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl wherein $R^{11}$ and $R^{13}$ or $R^9$ and $R^{15}$ or $R^9$ and $R^{11}$ or $R^{11}$ and $R^{15}$ or $R^9$ and $R^{13}$ may join together to form a bridging ring system wherein the two R groups together comprise of from 1 to 4 carbon atoms and wherein $R^9$ and $R^{10}$ or $R^{11}$ and $R^{12}$ or $R^{13}$ and $R^{14}$ or $R^{15}$ and $R^{16}$ may join to form a spiro ring system wherein the two R groups together comprise of from 1 to 5 carbon atoms;

$R^{17}$, $R^{18}$, $R^{19}$, $R^{20}$, and $R^{21}$ are each independently selected from the group consisting of hydrogen, halo, $NO_2$, $CF_3$, CN, $OR_{23}$, $SR_{23}$, $N(R_{23})_2$, $S(O)R_{22}$, $SO_2R_{22}$, $SO_2N(R_{23})_2$, $NR_{23}CO_2R_{22}$, $NR_{23}CON(R_{23})_2$, $COR_{23}$, $CO_2R_{23}$, $CON(R_{23})_2$, $NR_{23}SO_2R_{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR_{23}$, $SR_{23}$, $N(R_{23})_2$, $S(O)R_{22}$, and $SO_2R_{22}$ or wherein $R^{17}$ and $R^{18}$ may join together to form —CH=CH—CH=CH—, or wherein $R^{17}$ and $R^{18}$ or $R^{18}$ and $R^{19}$ or $R^{19}$ and $R^{20}$ or $R^{20}$ and $R^{21}$ may combine to form a saturated ring including from 3 to 6 carbon atoms wherein from 0 to 2 carbon atoms may be substituted with an oxygen atom;

$R_{22}$ is selected from the group consisting of $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl; and $R_{23}$ is selected from the group consisting of H, $C_{1-15}$ alkyl, aryl, or heteroaryl, wherein the alkyl and aryl substituents are optionally substituted with 1 substituent selected from the group consisting of halo, alkyl, mono- or dialkylamino, alkyl, CN, —O—$C_{1-6}$ alkyl, or $CF_3$.

In another embodiment, this invention is a substituted piperazine compound selected from the group consisting of N-(2,6-dimethylphenyl)-2-[4-(2-hydroxy-4-phenylbutyl) piperazinyl]acetamide; N-(2,6dimethylphenyl)-2-{4-[2-hydroxy-3-(2-methoxyphenyl)propyl]piperazinyl}- acetamide; 2-[4-(3-(2H-benzo[d]1,3-dioxolen-5-yl)-2-hydroxypropyl)piperazinyl]-N-(2,6-dimethylphenyl) acetamide; N-(2,6-dimethylphenyl)-2-{4-[2-hydroxy-3-(4-methoxyphenyl)propyl]piperazinyl}acetamide; N-(2,6-dimethylphenyl)-2-{4-[2-hydroxy-3-phenylpropyl] piperazinyl}acetamide; N-(2,6-dimethylphenyl)-2-{4-[4-(4-methoxyphenyl)-2-hydroxybutyl]piperazinyl}acetamide, 2-{4-[4-(2,6-difluorophenyl)-2-hydroxybutyl]piperazinyl}-N-(2,6-dimethylphenyl)acetamide, N-(2,6-dimethylphenyl)-2-{4-[4-(2-chlorophenyl)-2-hydroxybutyl]piperazinyl} acetamide, 2-(4-{4-[4-(tert-butyl)phenyl]-2-hydroxybutyl}piperazinyl)-N-(2,6-dimethylphenyl) acetamide, N-(2,6-dimethylphenyl)-2-{4-[4-(2-fluorophenyl)-2-hydroxybutyl]piperazinyl}acetamide, N-(2, 6-dimethylphenyl)-2-(4-{2-hydroxy-4-[4-(trifluoromethyl) phenyl]butyl}piperazinyl)acetamide, 2-[4-(3-(2H-benzo[d] 1,3-dioxolen-5-yl)-2-hydroxypropyl)piperazinyl]-N-(2,6-dimethylphenyl)-2-methylpropanamide, N-(2,6-dimethylphenyl)-2-[4-(2-hydroxy-3-phenylpropyl) piperazinyl]-2-methylpropanamide, N-(2,6-dimethylphenyl)-2-{4-[2-hydroxy-3-(3,4,5-trimethoxyphenyl)propyl]piperazinyl}-2-methylpropanamide, N-(2,6-dimethylphenyl)-2-[4-(2-hydroxy-5-phenylpentyl)piperazinyl]acetamide, N-(2,6-dimethylphenyl)-2-{4-[5-(2-fluorophenyl)-2-hydroxy-pentyl]piperazinyl}acetamide, and N-(2,6-dimethylphenyl)-2-{4-[5-(2-chlorophenyl)-2-hydroxy-pentyl] piperazinyl}acetamide.

In yet another embodiment, this invention is a method for administering one or more composition of this invention to a mammal in a treatment selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction.

DETAILED DESCRIPTION OF THE INVENTION

This invention concerns substituted piperazine compounds having the following formula:

I

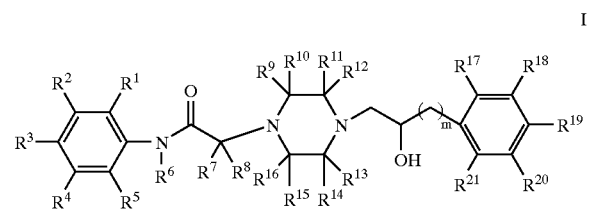

wherein m=0, 1 or 2 or 3;

$R^1$, $R^2$, $R^3$, $R^4$ and $R^5$ are each independently selected from the group consisting of hydrogen, halo, $NO_2$, $CF_3$, CN, $OR_{23}$, $SR_{23}$, $N(R_{23})_2$, $S(O)R_{22}$, $SO_2R_{22}$, $SO_2N(R_{23})_2$, $NR_{23}CO_2R_{22}$, $NR_{23}CON(R_{23})_2$, $COR_{23}$, $CO_2R_{23}$, CON $(R_{23})_2$, $NR_{23}SO_2R_{22}$, $C_{1-15}$ alkyl, $C_{2-15}$ alkenyl $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR_{23}$, $SR_{23}$, $N(R_{23})_2$, $S(O)R_{22}$, and $SO_2R_{22}$;

$R^6$, $R^7$ and $R_8$ each independently selected from the group consisting of hydrogen or $C_{1-15}$ alkyl;

$R^9$, $R_{10}$, $R^{11}$, $R^{12}$, $R^{13}$, $R^{14}$, $R^{15}$ and $R^{16}$ are each independently selected from the group consisting of hydrogen, $CO_2R_{23}$, $CON(R_{23})_2$, $C_{1-4}$ alkyl, or aryl wherein the alkyl and aryl substituents are optionally substituted with 1 substituent selected from the group consisting of halo, $CF_3$, CN, $OR_{23}$, $N(R_{23})_2$, $CO_2R_{23}$, $CON(R_{23})_2$ or aryl, wherein $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl wherein $R^{11}$ and $R^{13}$ or $R^9$ and $R^{15}$ or $R^9$ and $R^{11}$ or $R^{11}$ and $R^{15}$ or $R^9$ and $R^{13}$ may join together to form a bridging ring system wherein the two R groups together comprise of from 1 to 4 carbon atoms and wherein $R^9$ and $R^{10}$ or $R^{11}$ and $R^{12}$ or $R^{13}$ and $R^{14}$ or $R^{15}$ and $R^{16}$ may join to form a spiro ring system wherein the two R groups together comprise of from 1 to 5 carbon atoms;

$R^{17}$, $R^{18}$, $R^{19}$, $R^{20}$, and $R^{21}$ are each independently selected from the group consisting of hydrogen, halo, $NO_2$, $CF_3$, CN, $OR_{23}$, $SR_{23}$, $N(R_{23})_2$, $S(O)R_{22}$, $SO_2R_{22}$, $SO_2N$ $(R_{23})_2$, $NR_{23}CO_2R_{22}$, $NR_{23}CON(R_{23})_2$, $COR_{23}$, $CO_2R_{23}$, $CON(R_{23})_2$, $NR_{23}SO_2R_{22}$, $C_{1-15}$ alkyl, $C_{2-15}$ alkenyl, $C_{2-15}$ alkynyl, heterocyclyl, aryl, and heteroaryl, wherein the alkyl and aryl substituent are optionally substituted with 1 substituent selected from the group consisting of halo, $NO_2$, $CF_3$, CN, $OR_{23}$, $SR_{23}$, $N(R_{23})_2$, $S(O)R_{22}$, and $SO_2R_{22}$ or wherein $R^{17}$ and $R^{18}$ may join together may join together to form —CH=CH—CH=CH— or wherein $R^{17}$ and $R^{18}$ or $R^{18}$ and $R^{19}$ or $R^{19}$ and $R^{20}$ or $R^{20}$ and $R^{21}$ may combine to form a saturated ring including from 3 to 6 carbon atoms wherein from 0 to 2 carbon atoms may be substituted with an oxygen atom and wherein the ring may be optionally substituted with from 1 to 3 substituents selected from the group consisting of hydrogen, halo, $NO_2$, $CF_3$, CN, $OR^{23}$, $SR^{23}$, $N(R^{23})_2$, $S(O)R^{22}$, $SO_2R^{22}$, $SO_2N(R^{23})_2$, $NR^{23}CO_2R^{22}$, $NR^{23}CON(R^{23})_2$, $COR^{23}$, $CO_2R^{23}$, CON $(R^{23})_2$, $NR^{23}SO_2R^{23}$, $C_{1-15}$ alkyl, $C_{2-15}$ alkenyl, $C_{2-15}$ alkynyl, heterocyclyl, aryl, or heteroaryl, wherein the alkyl and aryl substituents are optionally substituted with 1 substituent selected from the group consisting of halo, $NO_2$, $CF_3$, CN, $OR^{23}$, $SR^{23}$, $N(R^{23})_2$, $S(O)R^{22}$, or $SO_2R^{22}$;

$R_{22}$ is selected from the group consisting of $C_{1-15}$ alkyl, aryl, or heteroaryl, wherein the alkyl and aryl substituents are optionally substituted with 1 substituent selected from the group consisting of halo, alkyl, monoalkylamino, dialkylamino, alkyl amide, aryl amide, heteroaryl amide, CN, O—$C_{1-6}$ alkyl, $CF_3$, or heteroaryl; and $R_{23}$ is selected from the group consisting of H, $C_{1-15}$ alkyl, aryl, or heteroaryl, wherein the alkyl and aryl substituents are optionally substituted with 1 substituent selected from the group consisting of halo, alkyl, mono- or dialkylamino, alkyl, CN, —O— $C_{1-6}$ alkyl, or $CF_3$.

In preferred compositions of this invention, m=0, 1 or 2 or 3; $R^1$, $R^2$, $R^3$, $R^4$ and $R^5$ are each independently selected from the group consisting of hydrogen, halo, $CF_3$, $OR_{22}$ and $C_{1-4}$ alkyl; $R^6$, $R^7$ and $R^8$ each independently selected from the group consisting of hydrogen and $C_{1-3}$ alkyl; $R^9$, $R^{10}$, $R^{11}$, $R^{12}$, $R^{13}$, $R^{14}$, $R^{15}$ and $R^{16}$ are each independently selected from the group consisting of hydrogen and $C_{1-4}$ alkyl, or $R^9$ and $R^{10}$ may together form a carbonyl, or $R^{11}$ and $R^{12}$ may together form a carbonyl, or $R^{13}$ and $R^{14}$ may together form a carbonyl, or $R^{15}$ and $R^{16}$ may together form a carbonyl, or wherein $R^{11}$ and $R^{13}$ or $R^9$ and $R^{15}$ or $R^9$ and $R^{11}$ or $R^{11}$ and $R^{15}$ or $R^9$ and $R^{13}$ may join together to form a ring including from 1 to 4 carbon atoms wherein $R^9$, $R^{10}$, $R^{11}$, $R^{12}$, $R^{13}$, $R^{14}$, $R^{15}$ and $R^{16}$ are not all hydrogen; and $R^{17}$, $R^{18}$, $R^{19}$, $R^{20}$ and $R^{21}$ are each independently selected from the group consisting of hydrogen, halo. $CF_3$, CN, $OR^{22}$, $S(O)R^{22}$, $SO_2R^{22}$, $SON(R^{22})_2$, $CON(R^{22})_2$, $C_{1-4}$ alkyl or $R^{17}$ and $R^{18}$ may together form —CH=CH—CH=CH—, and phenyl.

In other preferred compounds, $R^1$, $R^2$, $R^3$, $R^4$ and $R^5$ are each independently selected from the group consisting of hydrogen, halo, $CF_3$, $OR^{22}$ and $C_{1-2}$ alkyl wherein $R_{22}$ is a $C_{1-3}$ alkyl; $R^6$, $R^7$ and $R^8$ are each independently selected from the group consisting of hydrogen and methyl; $R^9$, $R^{10}$, $R^{11}$, $R^{12}$, $R^{13}$, $R^{14}$, $R^{15}$ and $R^{16}$ are each independently selected from the group consisting of hydrogen and $C_{1-2}$ alkyl, or $R^9$ and $R^{10}$ may together form a carbonyl, or $R^{15}$ and $R^{16}$ may together form a carbonyl with the proviso that $R^9$, $R^{10}$, $R^{11}$, $R^{12}$, $R^{13}$, $R^{14}$, $R^{15}$ and $R^{16}$ are not all simultaneously hydrogen and wherein $R^{11}$ and $R^{13}$ or $R^9$ and $R^{15}$ or $R^9$ and $R^{11}$ or $R^{11}$ and $R^{15}$ or $R^9$ and $R^{13}$ may join to form a ring including from 1 to 4 carbon atoms and $R^{17}$, $R^{18}$, $R^{19}$, $R^{20}$ and $R^{21}$ are each independently selected from the group consisting of hydrogen, halo, $CF_3$, CN, $OR^{22}$, and $C_{1-3}$ alkyl wherein $R^{22}$ is $C_{1-3}$ alkyl, and wherein $R^{17}$ and $R^{18}$ may together form a substituent selected from the group consisting of —CH=CH—CH=CH— and phenyl.

In still other preferred compounds, m=1 or 2; $R^1$, $R^2$, $R^3$, $R^4$ and $R^5$ are each independently selected from the group consisting of hydrogen, halo, $CF_3$, $OR^{22}$ and $C_{1-4}$ alkyl where $R^{22}$ is a $C_{1-3}$ alkyl; $R^6$, $R^7$, $R^8$, $R^9$, $R^{10}$, $R^{11}$, $R^{12}$, $R^{13}$, $R^{14}$, $R^{15}$ and $R^{16}$ are each independently selected from hydrogen and methyl; $R^{17}$, $R^{18}$, $R^{19}$, $R^{20}$ and $R^{21}$ are each independently selected from the group consisting of hydrogen, halo, $CF_3$, $OR^{22}$, $C_{1-3}$ alkyl where $R^{22}$ is methyl, or $R^{17}$ and $R^{18}$ may together form —CH=CH—CH=CH—, or $R^{18}$ and $R^{19}$ may together form —OCH$_2$O—.

In more preferred compounds, m=1 or 2; $R^1$, $R^2$, $R^3$, $R^4$, $R^5$, $R^6$, $R^7$ and $R^8$ each independently selected from methyl and hydrogen; $R^9$, $R^{10}$, $R^{11}$, $R^{12}$, $R^{13}$, $R^{14}$, $R^{15}$ and $R^{16}$ are each hydrogen; and $R^{17}$, $R^{18}$, $R^{19}$, $R^{20}$ and $R^{21}$ are each independently selected from the group consisting of hydrogen, halo, $CF_3$, $OR^{22}$ wherein $R^{22}$ is methyl, or $R^{17}$ and $R^{18}$ may together form —CH=CH—CH=CH—, or $R^{18}$ and $R^{19}$ may together form —OCH$_2$O—.

In yet other preferred compounds, m=1 or 2;; $R^1$ and $R^5$ are methyl; $R^2$, $R^3$, $R^4$, $R^6$, $R^7$, $R^8$, $R^9$, $R^{10}$, $R^{11}$, $R^{12}$, $R^{13}$, $R^{14}$, $R^{15}$ and $R^{16}$ are hydrogen; $R^{17}$, $R^{18}$, $R^{19}$, $R^{20}$ and $R^{21}$ are each independently selected from the group consisting of hydrogen, halo, $OR^{22}$ wherein $R^{22}$ is methyl, or $R^{17}$ and $R^{18}$ may together form —CH=CH—CH=CH—, or $R^{18}$ and $R^{19}$ may together form —OCH$_2$O—.

In still other preferred compounds, $R^1$ and $R^5$ are methyl; $R^2$, $R^3$, $R^4$, $R^6$, $R^7$, $R^8$, $R^9$, $R^{10}$, $R^{11}$, $R^{12}$, $R^{13}$, $R^{14}$, $R^{15}$ and $R^{16}$ are hydrogen; $R^{17}$ is selected from the group consisting of hydrogen, chloro, fluoro and methoxy; $R^{18}$ is selected from hydrogen and methoxy; $R^{19}$ is selected from hydrogen and methoxy; $R^{20}$ is hydrogen; $R^{21}$ is selected from hydrogen and chloro, or $R^{17}$ and $R^{18}$ may together form —CH=CH—CH=CH—, or $R^{18}$ and $R^{19}$ may together form —OCH$_2$O—.

Most preferably, the substituted piperazine compounds of this invention are selected from N-1 2,6-dimethylphenyl)-2-[4-(2-hydroxy4-phenylbutyl)piperazinyl]acetamide; N-(2,6-dimethylphenyl)-2-{4-[2-hydroxy-3-(2-methoxyphenyl)propyl]piperazinyl}acetamide; 2-[4(3-(2H-benzo[d]1,3-dioxolen-5-yl)-2-hydroxypropyl)piperazinyl]-N-(2,6-dimethylphenyl)acetamide; N-(2,6-dimethylphenyl)-2-{4-[2-hydroxy-3-(4-methoxyphenyl)propyl]piperazinyl}acetamide; N-(2,6-dimethylphenyl)-2-{4-[2-hydroxy-3-phenylpropyl]piperazinyl}acetamide, N-(2,6-dimethylphenyl)-2-{4-[4-(4-methoxyphenyl)-2-hydroxybutyl]piperazinyl}acetamide, 2-{4-[4-(2,6-difluorophenyl)-2-hydroxybutyl]piperazinyl}-N-(2,6-dimethylphenyl)acetamide, N-(2,6-dimethylphenyl)-2-{4-[4-(2-chlorophenyl)-2-hydroxybutyl]piperazinyl}acetamide, 2-(4-{4-[4-(tert-butyl)phenyl]-2-hydroxybutyl}piperazinyl)-N-(2,6-dimethylphenyl)acetamide, N-(2,6-dimethylphenyl)-2-{4-[4-(2-fluorophenyl)-2-hydroxybutyl]piperazinyl}acetamide, N-(2,6-dimethylphenyl)-2-(4-{2-hydroxy-4-[4-(trifluoromethyl)phenyl]butyl}piperazinyl)acetamide, 2-[4-(3-(2H-benzo[d]1,3-dioxolen-5-yl)-2-hydroxypropyl)piperazinyl]-N-(2,6-dimethylphenyl)-2-methylpropanamide, N2,6-dimethylphenyl)-2-[4-(2-hydroxy-3-phenylpropyl)piperazinyl]-2-methylpropanamide, N-(2,6-dimethylphenyl)-2-{4-[2-hydroxy-3-(3,4,5-trimethoxyphenyl)propyl]piperazinyl}-2-methylpropanamide, N-(2,6-dimethylphenyl)-2-[4(2-hydroxy-5-phenylpentyl)piperazinyl]acetamide, N-(2,6-dimethylphenyl)-2-{4-[5-(2-fluorophenyl)-2-hydroxypentyl]piperazinyl}acetamide, and N-(2,6-dimethylphenyl)-2-{4-[5-(2-chlorophenyl)-2-hydroxy-pentyl]piperazinyl}acetamide.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclobutyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2 to 4 carbon atoms with at least one, preferably 1–3, more preferably 1–2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkynyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'" R"", where R is lower alkyl, or substituted lower alkyl, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, quinolinyl, isoquinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, benzothiazolyl, benzoxazolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing from 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Optional" and "optionally" mean that the subsequently described event or circumstance may or may not occur, and that the description includes instances where the event or circumstance occurs and instances in which it does not. For example, "optional pharmaceutical excipients" indicates that a formulation so described may or may not include pharmaceutical excipients other than those specifically stated to be present, and that the formulation so described includes instances in which the optional excipients are present and instances in which they are not.

"Treating" and "treatment" refer to any treatment of a disease in a mammal, particularly a human, and include:

(i) preventing the disease from occurring in a subject which may be predisposed to the disease but has not yet been diagnosed as having it;
(ii) inhibiting the disease, i.e., arresting its development; or
(iii) relieving the disease, i.e., causing regression of the disease.

The compositions of this invention are useful for treating mammals in a therapy selected from the group consisting of protecting skeletal muscles against damage resulting from trauma, protecting skeletal muscles subsequent to muscle or systemic diseases such as intermittent claudication, to treat shock conditions, to preserve donor tissue and organs used in transplants, and to treat cardiovascular diseases including atrial and ventricular arrhythmias, Prinzmetal's (variant) angina, stable angina, and exercise induced angina, congestive heart disease, and myocardial infarction. The treatment is accomplished using a therapeutically effective amount of at least one compound of this invention and/or a pharmaceutically acceptable acid addition salt thereof in admixture with a pharmaceutically acceptable excipient.

Compounds falling within the scope of this invention include the optical isomers (+) and (−) and R- and S-isomers of the above-identified compounds and mixtures thereof. This invention includes the individual isomers and all possible mixtures thereof.

All of the aforementioned embodiments include the pharmaceutically acceptable acid addition salts thereof, particularly the mono and dihydrochlorides, and mixtures thereof.

The compounds having the general formula I can be prepared as outlined in Schemes 1–5. A general synthesis of the compounds of this invention is outlined in Scheme 1. Compound IV can be prepared by N-acylation of substituted anilines of general structure II with 2-substituted chloroacetylchloride III. Compound II is available commercially or readily prepared through reduction of the corresponding nitrobenzene derivative (acid/$SnCl_2$ or catalytic hydrogenation, see Advanced Organic Chemistry, Ed. J. March, (1992) A. Wiley-Interscience). Some examples of commercially available substituted anilines of general structure II include 2,6-dimethylaniline, 2,3-dimethylaniline, 2-methylaniline, 4-methylaniline, 2,4-dichloroaniline, 3,4-dichloroaniline, 2,5-dichloroaniline, 2,4-dichloroaniline, 2-chloroaniline, 3-chloroaniline, 2,6-difluoroaniline, 2,5-difluoroaniline, 3,4-difluoroaniline, 2-fluoroaniline, 4-fluoroaniline, 3-fluoroaniline, 2-fluoro-6-chloroaniline, 4-fluoro-3-chloroaniline.

SCHEME 1

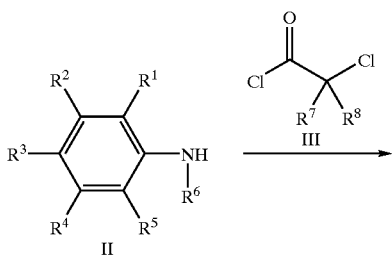

SCHEME 2

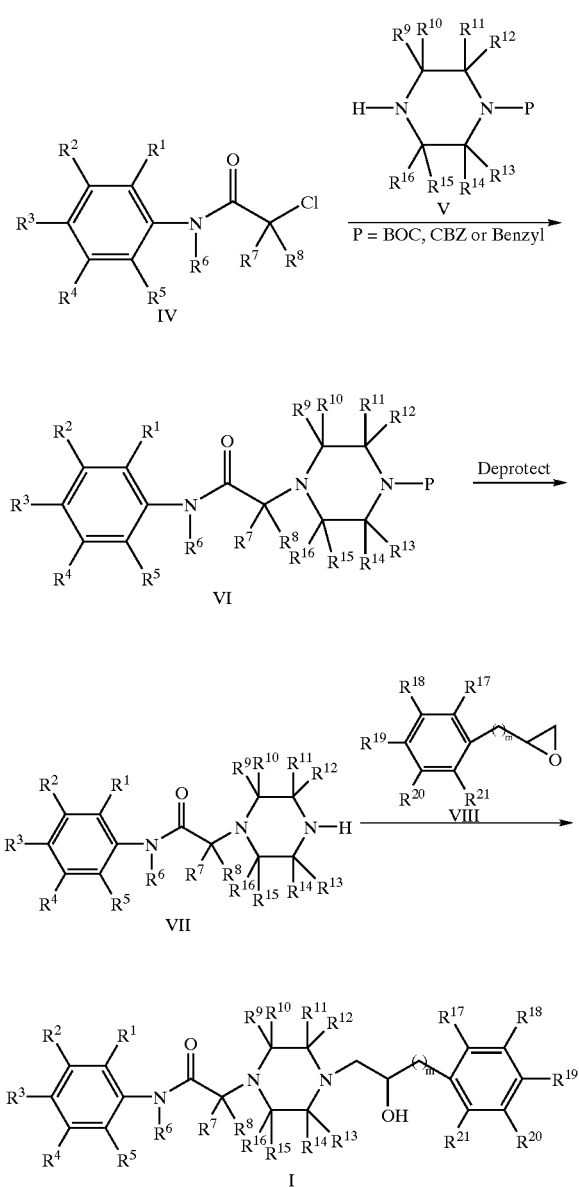

Epoxide VIII can be prepared as outlined in Scheme 2. Epoxidation of substituted allylbenzene XI using mCPBA or hydrogen peroxide can afford epoxide VIII (G. Majetich, R. Hicks, G. Sun and P. McGill, (1998), 63, 2564–2573). Compound XIA (n=1) in turn can be prepared by reacting aldehyde IX with methylenetriphenylphosphorane under Wittig conditions or Horner Emmons conditions [Advanced Organic Chemistry, Eds. J. March, (1992), Wiley-Interscience publication and S. Pine, G. Shen and H. Hoang, Synthesis, (1991), 1]. The compound XIB (n=2) can also be conveniently prepared by coupling a halide with the general formula X with allyl magnesium bromide. In some cases compound XI can be obtained from commercial sources. Examples of commercially available compounds corresponding to the general structure XI include (where m=0) 3-fluorostyrene, 4-fluorostyrene, 2-chlorostyrene, 3-chlorostyrene, 4-chlorostyrene, 2,6-dichlorostyrene, 3,4-dichlorostyrene and 3,4-dimethoxystyrene. Other examples of commercially available compounds with the general structure XI include (where m=1) 4-methoxyallylbenzene, 2-hydroxyallylbenzene, 4,5-dimethoxyallylbenzene, 2-methylallylbenzene safrole and 1-allylnaphthalene.

Compound VI can be obtained by reacting compound IV with a N-protected substituted piperazine V through warming in an appropriate solvent (e.g. DMF, EtOH). Protection of the nitrogen of compound V is only required when it is useful to control the regiochemistry of the addition of Compound V with compound IV. In some cases, compound V can be obtained from commercial sources. Examples of commercially available compounds of general structure V include 2-methyl piperazine, 2,5-dimethyl piperazine and 2,6-dimethyl piperazine. Deprotection of compound VI can be accomplished using the standard conditions (e.g. for Boc group use TFA, for CBZ and benzyl use hydrogenation). Compound I can be prepared by reacting compound VII with epoxide VIII through warming in an appropriate solvent (ethanol, DMF).

SCHEME 3

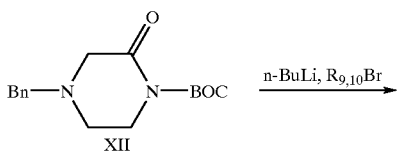

-continued

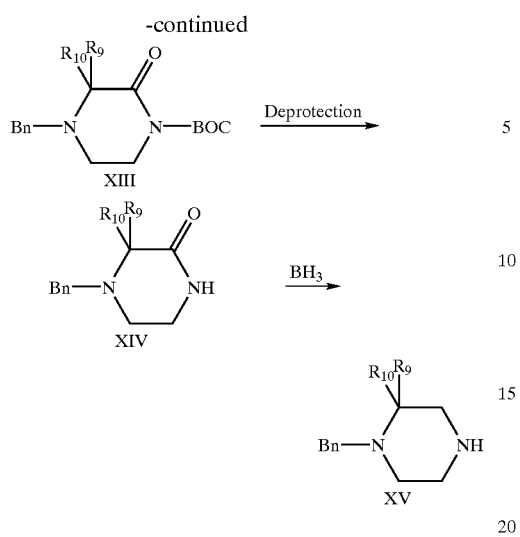

Compound V can be prepared as described in Scheme 3. Alkylation of compound XII with alkyl halides using t-BuLi as base can afford compound XIII as described by Pohlman et. al. (J. Org. Chem, (1997), 62, 1016–1022). Reduction of XIII using diborane can afford N-benzyl protected version of compound V after N-Boc deprotection with trifluoroacetic acid (TFA, for the diborane reduction see Jacobson et. al, J. Med. Chem, (1999), 42, 1123–1144).

SCHEME 4

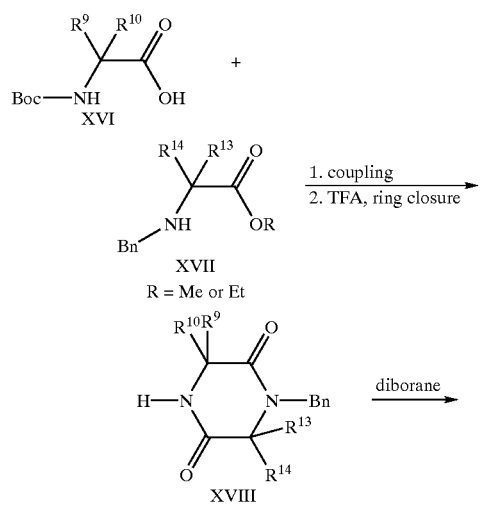

Compound V can also be prepared through standard coupling (eg. EDC or PyBroP) of D or L amino acids and standard deprotection (e.g., Boc removal by TFA treatment) as outlined in Scheme 4 [For preparations of diketopiperazines see—P. Cledera et al. Tetrahedron, (1998) p. 12349–12360 and R. A. Smith et al Bioorg. Med. Chem. Lett. (1998) p. 2369–2374]. Reduction of the diketopiperazine with diborane can afford the N-benzyl protected version of compound V.

Compound V also includes the bicyclic homologs of piperazine (1S,4S)-(+)-2,5-diazabicyclo[2.2.1]heptane 83, 3,8-diazabicyclo[3.2.1] octane 84, and 2,5-diazabicyclo[2.2.2] octane 85.

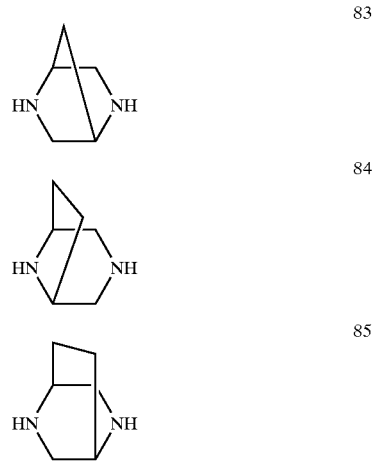

Commercially available bicyclic analogs include (1S,4S)-(+)-2,5-diazabicyclo[2.2.1]heptane 83. Compounds 84, 85, and the (1R,4R) isomer of 83 can be prepared by published procedures (for 84 and 85—see Sturm, P. A. et al, J. Med. Chem. 1974, 17, 481–487; for 83 see—Barish, T. F. and Fox, D. E. J. Org. Chem., 1990, 55, 1684–1687).

A specific example of the preparation of a compound from this invention is disclosed in Scheme 5 to further illustrate how to prepare the compounds of this invention. In particular, 2,6-dichloroaniline was acylated with 2-chloroacetyl chloride 2 using saturated bicarbonate and ether (1:1) as base and co-solvent, respectively to afford the chloroacetamide derivative 3. Further reaction of compound 3 with piperazine afforded compound 5 through warming in ethanol. Reaction of compound 5 with epoxide 6 by warming both components in ethanol at reflux afforded piperazine derivative 7.

SCHEME 5

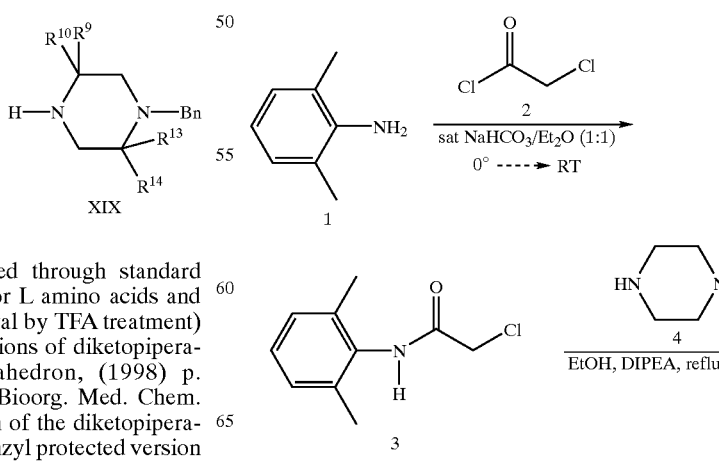

-continued

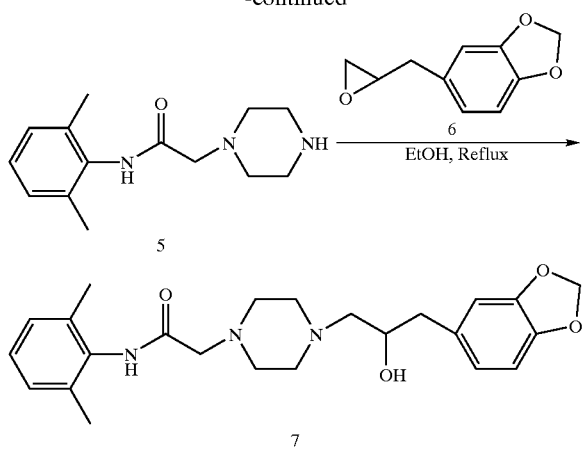

Compound 8 is commercially available and was epoxidized using 3-chloroperoxybenzioc acid in dichloromethane as illustrated in Scheme 6.

SCHEME 6

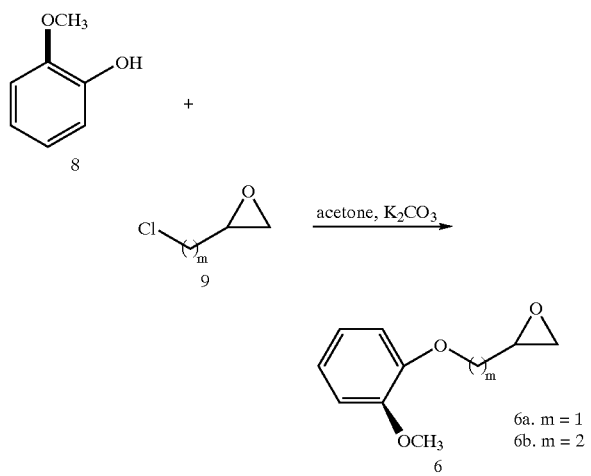

Four carbon epoxide 15 can be prepared by coupling commercially available 4-methoxybenzyl chloride with allylmagnesium bromide followed by oxidation with mCPBA as illustrated in scheme 7.

SCHEME 7

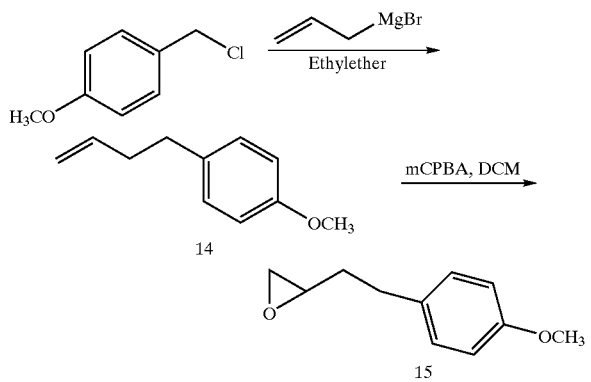

The acid addition salts of the compounds of this invention may be converted to the corresponding free base by treating with a suitable base, such as potassium carbonate or sodium hydroxide, typically in the presence of aqueous solvent, and at a temperature of between about 0 degrees C. and 100 degrees C. The free base form is isolated by conventional means, such as extraction with an organic solvent.

Salts of the compounds of this invention may be interchanged by taking advantage of differential solubilities and volatilities, or by treating with the appropriately loaded ion exchange resin. This conversion is carried out at a temperature between about 0° C. and the boiling point of the solvent being used as the medium for the procedure. Administration of the active compounds and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parentarally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions may include one or more conventional pharmaceutical excipients and at least one active compound of this invention or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgment of the prescribing physician. However, an effective dosage is in the range of 0.1–30 mg/kg/day, preferably 0.5–20 mg/kg/day. For an average 70 kg human, this would amount to 7–2100 mg per day, or preferably 35–1400 mg/day. Since many of the effects of the compounds herein (protect skeletal muscles against damage resulting from trauma; protect skeletal muscles subsequent to muscle or systemic diseases such as intermittent claudication; treat shock conditions; preserve donor tissue and organs used in transplants; and treat cardiovascular diseases including atrial and ventricular arrhythmias, Prinzmetal's (variant) angina, stable angina, exercise induced angina, congestive heart disease, and myocardial infarction) are achieved through a similar mechanism (partial fatty acid oxidation inhibition) dosages (and forms of administration) are all generally within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s), a therapeutically effective amount, i.e. in an amount effective to alleviate the symptoms of the subject being treated. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%-95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. In another recent approach, the compositions of this invention can be administered orally in a sustained release dosage form using the compositions and/or methods disclosed in U.S. patent application Ser. No. 09/321,522, filed on May 27, 1999, the specification of which is incorporated herein by reference.

It is within the scope of this invention to administer one or more compounds of this invention to a mammal, and preferably to a human by other known routes of pharmaceutical dosage form administration including, but not limited to by bolus, intravenously, transdermally, through inhalation, sub-cutaneously, or any other therapeutic agent administration method or route know to one skilled in the art.

The following Examples are representative of the invention, but are not to be construed as limiting the scope of the claims.

EXAMPLE 1

2-[4-(3-Benzo[1,3]dioxol-5-yl-2-hydroxy-propyl)-piperazin-1-yl]-N-(2,6-dimethyl-phenyl)-acetamide (7)

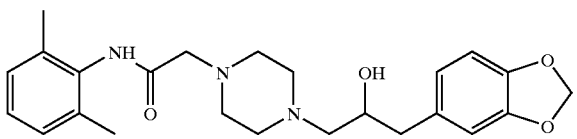

Part A
Synthesis of N-(2,6dimethylphenyl)-2-chloroacetamide (3).
2,6-dimethylaniline (9.8 g, 81.2 mmol) was dissolved in ether (100 mL) and saturated aqueous NaHCO₃ (100 mL) and the reaction mixture was cooled in an ice/water bath. To the cold solution was added chloroacetyl chloride 2 (9.17 g, 81.2 mmol) dropwise over a period of 2 h. The mixture was allowed to warm to RT over 14 h. The mixture was extracted with EtOAc (3×50). The combined organic layers were dried over MgSO₄, filtered and concentrated. The residue was triturated in ether and filtered to afford compound 3 as a white solid.

Part B
Synthesis of N-(2,6-dimethylphenyl)-2-piperazinylacetamide (5).
To a solution of compound 3 (5 g, 25.2 mmol) in ethanol (100 mL,) was added compound 4 (2.1 g, 25.0 mmol) and N,N-diisopropylamine (3.2 g, 25.2 mmol). The reaction mixture was refluxed for 24 h. The mixture was concentrated in vacuo and the residue was purified by column chromatography (10:1 dichloromethane:methanol) to afford compound 5.

Part C
Synthesis of 5-(oxiran-2-ylmethyl)-2H-benzo[d]1,3-dioxane (6).
To an ice cold solution of 8 (1.0 g, 6.17 mmol) in dichloromethane was added dropwise a solution of 3-chloroperoxybenzoic acid (1.8 g, 10.43 mmol) in 20 mL dichloromethane over a period of 1 h. The reaction mixture was allowed to stir at RT for 12 h. The reaction mixture was filtered to remove any solids and concentrated in vacuo. To the residue was added diethyl ether (200 ml), and it was washed with saturated sodium bicarbonate (3×100 ml). The organic layer was dried over MgSO₄, and concentrated in vacuo. The residue was purified using Prep. TLC (2:1 hexane:ethyl acetate) to yield 6.

Part D
2-[4-(3-(2H-benzo[d]1,3-dioxolen-5-yl)-2-hydroxypropyl)piperazinyl]-N-(2,6-dimethylphenyl) acetamide (7)
To a solution of compound 5 (0.4 g, 1.64 mmol) in ethanol (100 mL) was added compound 6 (0.38 g, 2.14 mmol) in 10 mL EtOH. The reaction mixture was refluxed for 24 h. The mixture was concentrated in vacuo, and the residue was purified by using Prep. TLC (10:1 dichloromethane:methanol) to afford compound 7:Mass spectrum (MH+1)=426.34.

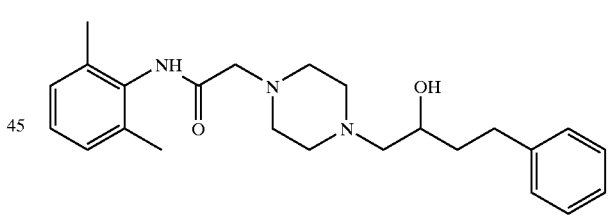

N-(2,6-dimethylphenyl)-2-[4-(2-hydroxy-4-phenylbutyl)piperazinyl]acetamide (9).
Compound 9 was prepared in the manner of compound 7 substituting 4-phenyl-butene for 3-(3,4-methylendioxyphenyl)-1-propene in part C to afford compound 9: Mass spectrum (MH+1)=396.32.

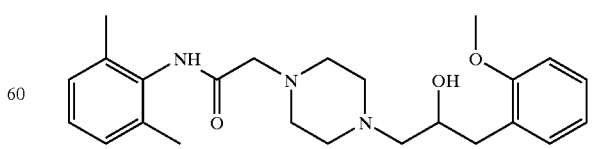

N-(2,6-dimethylphenyl)-2-{4-[2-hydroxy-3(2-methoxyphenyl)-propyl]piperazinyl}acetamide (10)
Compound 10 was prepared in the manner of compound 7 substituting 3-(2-methoxyphenyl)-1-propene for 3-(3,4- methylendioxyphenyl)-1-propene in part C to afford compound 10:Mass spectrum (MH+1)=412.35.

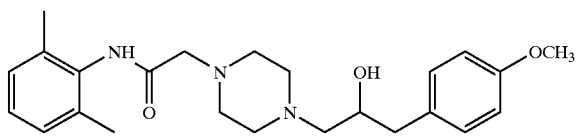

N-(2,6-dimethylphenyl)-2-{4-[2-hydroxy-3-(4-methoxyphenyl)propyl]piperazinyl}acetamide (11).
Compound 11 was prepared in the manner of compound 7 substituting 3-(4-methoxyphenyl)-1-propene for 3-(3,4-methylendioxyphenyl)-1-propene in part C to afford compound 11: Mass spectrum (MH+1)=412.35.

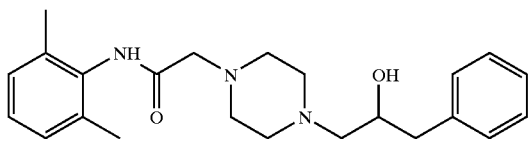

N-(2,6-dimethylphenyl)-2-{4-[2-hydroxy-3-phenylpropyl]piperazinyl}acetamide (12)
Compound 12 was prepared in the manner of compound 7 substituting 3-phenyl-1-propene for 3-(3,4-methylendioxyphenyl)-1-propene in part C to afford compound 12:Mass spectrum (MH+1)=382.

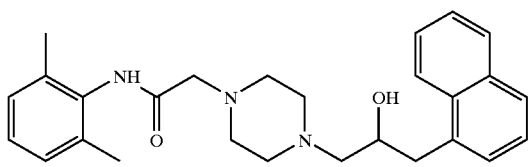

N-(2,6-dimethylphenyl)-2-[4-(2-hydroxy-3-naphthylpropyl)piperazinyl]acetamide (13).
Compound 13 was prepared in the manner of compound 7 substituting 3-(1-naphthyl)-1-propene for 3-(3,4-methylendioxyphenyl)-1-propene in part C to afford compound 13:Mass spectrum (MH+1)=432.55.

Part A
Intermediate (14): To a solution of 4-methoxybenzyl chloride (2-mmol) in anhydrous ether (10 mL), was added allylmagnesium bromide (4 mL, 1M solution in THF) and the reaction mixture was allowed to stir for 16 h at room temperature. Sat. ammonium chloride solution 91 mL) was added and the ether layer was separated, washed with water and dried. Evaporation of ether under reduced pressure afforded olefin 14 as an oil. It was used in the next reaction without purification.

Part B
Intermediate (15): To an ice cold solution of 15 (2 mmol) in dichloromethane was added dropwise a solution of 3-chloroperoxybenzoic acid (4 mmol) in 20 mL dichloromethane over a period of 1 h. The reaction mixture was allowed to stir at RT for 12 h. The reaction mixture was filtered to remove any solids and concentrated in vacuo. To the residue was added diethyl ether (200 ml), and it was washed with saturated sodium bicarbonate (3×100 ml). The organic layer was dried over MgSO$_4$, and concentrated in vacuo. The residue was purified using Prep. TLC (2:1 hexane: ethyl acetate) to yield 15.

Part C

Synthesis of N-(2,6-dimethylphenyl)-2-{4-[4-(4-methoxyphenyl)-2-hydroxybutyl]piperazinyl}acetamide (16)

To a solution of compound 5 (0.4 g, 1.64 mmol) in ethanol (100 mL) was added compound 15 (2.14 mmol) in 10 mL EtOH. The reaction mixture was refluxed for 24 h. The mixture was concentrated in vacuo, and the residue was purified by using Prep. TLC (10:1 dichloromethane:methanol) to afford compound 16. (M+1)=426.3

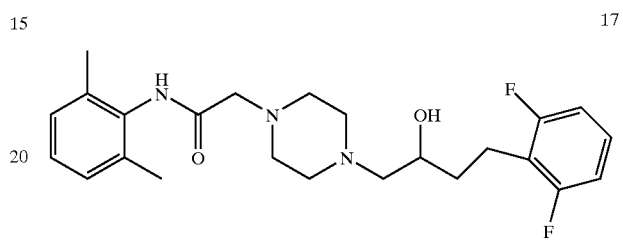

2-{4-[4-(2,6-difluorophenyl)-2-hydroxybutyl]piperazinyl}-N-(2,6-dimethylphenyl)acetamide(17)

Compound 17 was prepared in a manner similar to that of compound 16 substituting 2,6-difluorobenzyl chloride for 4-methoxybenzyl chloride. (M+1)=432.2

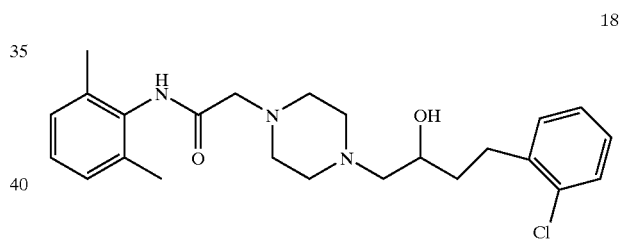

N-(2,6-dimethylphenyl)-2-{4-[4-(2-chlorophenyl)-2-hydroxybutyl]piperazinyl}acetamide(18)

Compound 18 was prepared in a manner similar to that of compound 16 substituting 2-chlorobenzyl chloride for 4-methoxybenzyl chloride. (M+1)=430.2

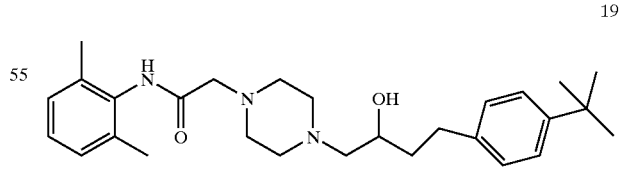

2-(4-{4-[4-(tert-butyl)phenyl]-2-hydroxybutyl}piperazinyl)-N-(2,6-dimethylphenyl)acetamide(19)

Compound 19 was prepared in a manner similar to that of compound 16 substituting 4-t-butylbenzyl chloride for 4-methoxybenzyl chloride. (M+1)=452.3

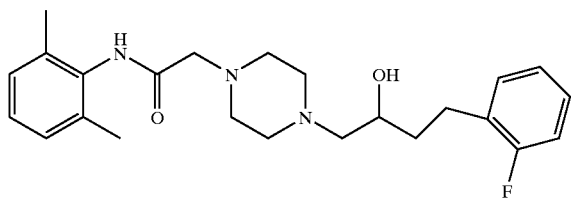

20

N-(2,6-dimethylphenyl)-2-{4-[4-(2-fluorophenyl)-2-hydroxybutyl]piperazinyl}acetamide(20)

Compound 20 was prepared in a manner similar to that of compound 16 substituting 2-fluorobenzyl chloride for 4-methoxybenzyl chloride. (M+1)=414.2

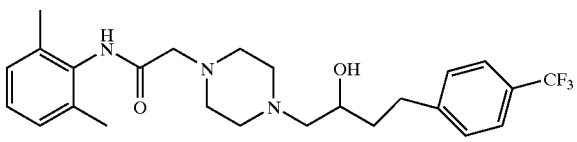

21

N-(2,6-dimethylphenyl)-2-(4-{2-hydroxy-4-[4-(trifluoromethyl)phenyl]butyl}piperazinyl)acetamide(21)

Compound 21 was prepared in a manner similar to that of compound 16 substituting 4-trifluoromethylbenzyl chloride for 4-methoxybenzyl chloride. (M+1)=464.2

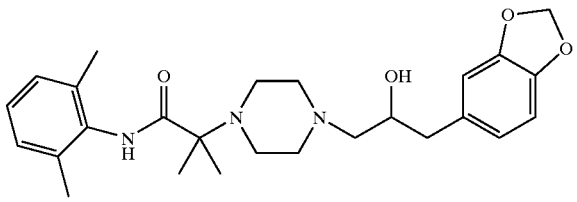

22

2-[4-(3-Benzo[1,3]dioxol-5-yl-2-hydroxy-propyl)-piperazin-1-yl]-N-(2,6-dimethyl-phenyl-isobutyramide (22)

This compound was prepared in a manner similar to that of 7, substituting 2-chloro-2-methylpropionyl chloride for chloroacetyl chloride in part A. (M+1)=454.54

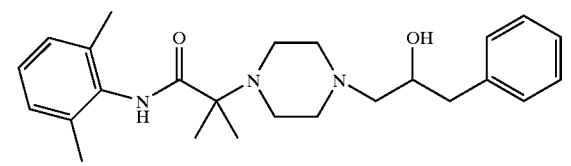

23

N-(2,6-Dimethyl-phenyl)-2-[4-(2-hydroxy-3-phenyl-propyl)-piperazin-1-yl]-isobutyramide (23)

This compound was prepared in a manner similar to that of 7, substituting 2-chloro-2-methylpropionyl chloride for chloroacetyl chloride in part A and allylbenzene for 8. (M+1)=410.34.

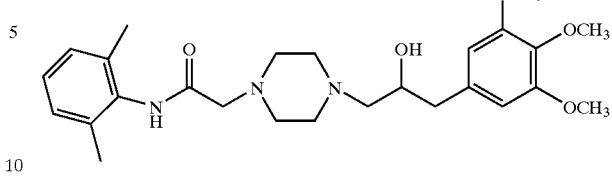

24

N-(2,6-dimethylphenyl)-2-{4-[2-hydroxy-3-(3,4,5-trimethoxyphenyl)prophyl]piperazinyl}acetamide (24)

This compound was prepared in a manner similar to that of 7, substituting 2-chloro-2-methylpropionyl chloride for chloroacetyl chloride in part A and 3,4,5-trimethoxy allybenzene for 8. (M+1)=472.54

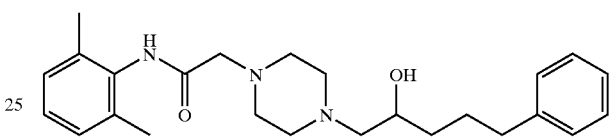

25

N-(2,6-dimethylphenyl)-2-[4-(2-hydroxy-5-phenylpentyl)piperazinyl]acetamide (25)

This compound was prepared in a manner similar to that of 16, substituting phenethyl chloride for 4-methoxybenzyl chloride in part A. (M+1)=410.4.

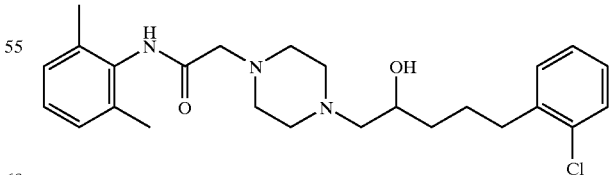

26

N-(2,6-dimethylphenyl)-2-{4-[5-(2-fluorophenyl)-2-hydroxy-pentyl]piperazinyl}acetamide(26)

This compound was prepared in a manner similar to that of 16, substituting 2-fluorophenethyl chloride for 4-methoxybenzyl chloride in part A. (M+1)=428.1.

27

N-(2,6-dimethylphenyl)-2-{4-[5-(2-chlorophenyl)-2-hydroxy-pentyl]piperazinyl}acetamide(27)

This compound was prepared in a manner similar to that of 16, substituting 2-chlorophenethyl chloride for 4-methoxybenzyl chloride in part A. (M+1)=444.3

EXAMPLE 2

Mitochondrial Assays

Rat heart mitochodria were isolated by the method of Nedergard and Cannon (Methods in Enzymol. 55, 3, 1979).

Palmitoyl CoA oxidation—The Palmitoyl CoA oxidation was carried out in a total volume of 100 microliters containing the following agents: 110 mM KCl, 33 mM Tris buffer at pH 8, 2 mM KPi, 2 mM $MgCl_2$, 0.1 mM EDTA, 14.7 microM defatted BSA, 0.5 mM malic acid, 13 mM carnitine, 1 mM ADP, 52 micrograms of mitochondrial protein, and 16 microM 1-C14 palmitoyl CoA (Sp. Activity 60 mCi/mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion. The data are presented as % activity of control.

TABLE 1

Inhibition of mitochondrial fatty acid oxidation using palmitoyl CoA as substrate – % of Control at 3 concentrations.

| Compound # | 100 μM | 30 μM | 3 μM |
|---|---|---|---|
| Ranolazine | 75% | 90% | — |
| 9 | 84% | 84% | — |
| 10 | — | — | — |
| 7 | — | — | — |
| 11 | 83% | 92% | — |
| 12 | 42% | 95% | — |
| 13 | — | — | — |
| 16 | 37% | | |
| 17 | 78% | | |
| 18 | 78% | | |
| 19 | 35% | | |
| 20 | 56% | | |
| 21 | 56% | | |
| 24 | 72% | | |

EXAMPLE 3

Palmitoyl Carnitine Oxidation—The Palmitoyl carnitine oxidation was carried out in a total volume of 100 microliters containing the following agents: 110 mM KCl, 33 mM Tris buffer at pH 8, 2 mM KPi, 2 mM $MgCl_2$, 0.1 mM EDTA, 0.1mg/ml of defatted BSA, 0.5 mM malic acid, 3 mM ADP, 52 micrograms of mitochondrial protein, and 43 microM 1-C14 palmitoyl carnitine (Sp. Activity 60 mCi/ mmole; 20 microCi/ml, using 5 microliters per assay). The compounds of this invention were added in a DMSO solution at the following concentrations: 100 microM, 30 microM, and 3 microM. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion. The data are presented as % activity of control.

TABLE 2

Inhibition of mitochondrial fatty acid oxidation using palmitoyl carnitine as substrate – % of Control at 3 concentrations.

| Compound # | 100 μM | 30 μM | 3 μM |
|---|---|---|---|
| Ranolazine | 63% | 98% | — |
| 9 | — | — | — |
| 10 | — | — | — |
| 7 | — | — | — |
| 11 | — | — | — |
| 12 | 56% | — | — |
| 13 | — | — | — |

EXAMPLE 4

Metabolic Stability: As a measure of metabolic stability the compounds of this invention were incubated with human liver S-9 microsomal fractions. After, 30 minutes at 37 C., the amount of parent drug remaining was determined using LC-mass spec. The response factors for each compound was determined by establishing a standard curve and using an internal standard during the analysis of the samples. An average of five experiments for percentage of ranolazine remaining at the 30 minute time point is 57%. The compounds of this invention were assayed as described in the protocol below and the percentage of parent remaining was divided by the average % of ranolazine remaining (57%) affording a metabolic stability factor. A compound with a stability number greater than 1.2 has a better stability than ranolazine in the liver S-9 assay. A compound with a stability number between 1.2 and 0.8 has an equivalent stability in the liver S-9 assay. A compound with a stability number less than 0.8 is less stable than ranolazine in the liver S-9 assay.

The purpose of this experiment is to compare the percentages remaining for compounds of this invention with the percentage remaining for ranolazine after 30 minutes of incubation with human liver S9 fractions.

Reagents:

The following reagents were used; Potassium phosphate, 0.5M pH 74. (incubation buffer), kept at room temperature; 0.05M $MgCl_2$ kept at 4° C.; β-Nicotinamide adenine dinucleotide phosphate, tetrasodium salt, reduced form (NADPH), 0.02M solution in water (~16.6 mg/mL) from Sigma Lot # 79H7044 prepared on day of use. 1 mM of ranolazine or Compounds 7, 9, and 10–13 in ACN further diluted to obtain 100 μM in 10% ACN; Human S9 stock: 20 mg/mL from Gentest Lot 3.

Procedure:

Incubation mixtures were prepared as follows:

TABLE 3

| Component | Volume per 0.25 mL of Incubation Mixture | Final concentration |
|---|---|---|
| 100 μM CVT compounds | 25 μL | 10 μM |
| $MgCl_2$ | 25 μL | 0.005 M |
| NADPH | 25 μL | 0.002 M |
| S9 | 25 μL | 2 mg/mL |

TABLE 3-continued

| Component | Volume per 0.25 mL of Incubation Mixture | Final concentration |
|---|---|---|
| Incubation Buffer | 25 μL | 0.05 M |
| Water | 125 μL | — |

*1% organic solvent (acetonitrile) was used in incubation mixture.
Generally, 30 incubates were prepared at a time by pre-mixing 0.75 mL of MgCl$_2$, 0.75 mL of incubation buffer, 0.75 mL of NADPH, 3.75 mL of water. Then pipette 200 μL/incubate, add 25 μL of compound being tested, mix, and initiate reaction by addition of S-9.

Combine all components with incubation buffer and re-pipette 200 μL/tube+25 μL of the compound being tested along with 25 μL of S-9.

After 5 min of pre-incubation at 37° C., at 0 and 30 min after starting the reaction, a 50 μl aliquot of the incubation mixture was removed and added to 100 μL of 9:1 acetonitrile: methanol containing the internal standard.

The mixture was centrifuged and a 100 μL aliquot of the supernatant was diluted in 1 mL of solvent C (0.1% Formic Acid in water). Then samples were analyzed for change between the ratio of compound to internal standard at time zero and 30 minutes by LC/MS (injected 10 μL).

Analytical and Data Calculations:

Samples were analyzed for the starting compounds and potential metabolite/s by LC/MS using an internal standard on a Micromass platform mass spec with a Keystone Inc. BDS ODS-C18 column with a flow rate of 0.25 ml/min. Following the above procedure resulted in the following relative stability factors as compared to ranolazine for the compounds of this invention as illustrated in Table 4.

TABLE 4

| Compound # | Liver S-9 stability factor |
|---|---|
| Ranolazine | 1.0 |
| 9 | 1.18 |
| 10 | 1.03 |
| 7 | 1.46 |
| 11 | 1.33 |
| 12 | 1.38 |
| 13 | 0.10 |
| 16 | 0.99 |
| 17 | 0.71 |
| 18 | 0.68 |
| 19 | — |
| 20 | — |
| 21 | — |
| 22 | 1.49 |
| 23 | 0.5 |
| 24 | 1.05 |
| 25 | — |
| 26 | — |
| 27 | — |

What we claim is:

1. A substituted piperazine compound having the following formula:

I

[Structural formula showing a substituted piperazine compound with substituents $R^1$ through $R^{21}$]

wherein m=1 or 2 or 3;

$R^1$, $R^2$, $R^3$, $R^4$ and $R^5$ are each independently selected from the group consisting of hydrogen, halo, $CF_3$, $OR_{23}$, and straight or branched $C_{1-6}$ alkyl $R^6$, $R^7$ and $R^8$ each independently selected from the group consisting of hydrogen and straight or branched $C_{1-5}$ alkyl;

$R^9$, $R^{10}$, $R^{11}$, $R^{12}$, $R^{13}$, $R^{14}$, $R^{15}$ and $R^{16}$ are hydrogen;

$R^{17}$, $R^{18}$, $R^{19}$, $R^{20}$, and $R^{21}$ are each independently selected from the group consisting of hydrogen, halo, and straight or branched $C_{1-6}$ alkyl; or $R^{19}$ and $R^{20}$ may combine to form a saturated ring having 5 carbon atoms wherein 2 carbon atoms may be substituted with an oxygen atom or wherein $R^{17}$ and $R^{18}$ or $R^{18}$ and $R^{19}$ may together form a ring selected from the group consisting of —CH=CH—CH=CH— and —O—CH$_2$—O—; and $R_{23}$ is selected from the group consisting of straight or branched, $C_{1-6}$ alkyl.

2. The compound of claim 1 wherein; $R^6$ is hydrogen and $R^7$ and $R^8$ each independently selected from the group consisting of hydrogen or methyl.

3. The compound of claim 2 wherein $R^{17}$, $R^{18}$, $R^{19}$, $R^{20}$, and $R^{21}$, are each independently selected from the group consisting of hydrogen, halo, $C_{1-4}$ straight or branched alkyl, or $R^{19}$ and $R^{20}$ may combine to form a saturated ring including having from 5 carbon atoms wherein 2 carbon atoms may be substituted with an oxygen atom or $R^{17}$ and $R^{18}$ may together form —CH=CH—CH=CH—.

4. The compound of claim 2 wherein $R^{17}$, $R^{18}$, $R^{19}$, $R^{20}$, and $R^{21}$ are each independently selected from the group consisting of hydrogen, halo, $C_{1-4}$ alkyl, straight or branched alkyl, or $R^{19}$ and $R^{20}$ may combine to form —O—CH$_2$—O— or —OCH$_2$CH$_2$O— or $R^{17}$ and $R^{18}$ may together form —CH=CH—CH=CH—.

5. The compound of claim 1 wherein m=1 or 2;

$R^1$, $R^2$, $R^3$, $R^4$ and $R^5$ are each independently selected from the group consisting of hydrogen, halo, $CF_3$, $OR^{23}$ and $C_{1-2}$ alkyl wherein $R_{23}$ is a $C_{1-2}$ alkyl;

$R^6$, $R^7$ and $R^8$ each independently selected from the group consisting of hydrogen and methyl; and $R^{17}$, $R^{18}$, $R^{19}$, $R^{20}$, and $R^{21}$ are each independently selected from the group consisting of hydrogen, halo, $C_{1-3}$ straight or branched alkyl or $R^{17}$ and $R^{18}$ or $R^{18}$ and $R^{19}$ may together form a ring selected from the group consisting of —CH=CH—CH=CH—, —O—CH$_2$—O, and —O—CH$_2$—CH$_2$—O—.

6. The compound of claim 5 wherein $R^6$, $R^7$ and $R^8$ are each hydrogen.

7. The compound of claim 5 wherein $R^{17}$ and $R^{18}$ or $R^{18}$ and $R^{19}$ together form a ring selected from the group consisting of —CH=CH—CH=CH—, —O—CH$_2$—O.

8. The compound of claim 1 wherein m=1 or 2;

$R^6$, $R^7$ and $R^8$ are each hydrogen;

$R^{17}$, $R^{18}$, $R^{19}$, $R^{20}$ and $R^{21}$ are each independently selected from the group consisting of hydrogen, halo, $C_{1-4}$ straight or branched alkyl.

9. The compound of claim 8 wherein, $R^{17}$, $R^{18}$, $R^{19}$, $R^{20}$, and $R^{21}$ are each selected from the group consisting of hydrogen, Cl, F, and $C_{1-4}$ straight or branched alkyl.

10. The compound of claim 9 wherein $R^{18}$, and $R^{20}$ are each hydrogen.

11. The compound of claim 8 wherein, $R^{17}$, $R^{18}$, $R^{20}$ and $R^{21}$ are each hydrogen and $R^{19}$ is selected from the group consisting of F, $C_{1-4}$ straight or branched alkyl.

12. A method of treatment comprising administering a therapeutically effective amount of a compound of claim 1 to a mammal in need of a treatment selected from the group consisting of protecting skeletal muscles against damage resulting from trauma, protecting skeletal muscles subsequent to muscle or systemic diseases, treating shock conditions, preserving donor tissue and organs used in transplants, or treating cardiovascular diseases.

13. The method of claim 12 wherein the cardiovascular disease is selected from the group consisting of atrial and ventricular arrhythmias, Prinzmetal's (variant) angina, stable angina, exercise induced angina, congestive heart disease, or myocardial infarction.

14. The method of claim 12 wherein the therapeutically effective amount ranges from about 0.01 to about 100 mg/kg weight of the mammal.

15. The method of claim 12 wherein the mammal is a human.

16. A pharmaceutical composition of matter comprising the compound of claim 1 and one or more pharmaceutical excipients.

17. The pharmaceutical composition of claim 16 wherein the pharmaceutical composition is in the form of a solution.

18. The pharmaceutical composition of claim 16 wherein the pharmaceutical composition is in a form selected from the group consisting of a tablet or a capsule.

* * * * *